US011049608B2

United States Patent
Yardley et al.

(10) Patent No.: US 11,049,608 B2
(45) Date of Patent: Jun. 29, 2021

(54) 3D AUGMENTED REALITY DOCUMENT INTERACTION

(71) Applicant: H&R Accounts, Inc., Moline, IL (US)

(72) Inventors: Jayson Yardley, Moline, IL (US); Olivier Witteveen, Moline, IL (US); Pete Hamlin, Moline, IL (US); Christine Hanson-Ehlinger, Moline, IL (US)

(73) Assignee: H&R Accounts, Inc., Moline, IL (US)

( * ) Notice: Subject to any disclaimer, the term of this patent is extended or adjusted under 35 U.S.C. 154(b) by 60 days.

(21) Appl. No.: 16/502,351

(22) Filed: Jul. 3, 2019

(65) Prior Publication Data

US 2020/0013499 A1    Jan. 9, 2020

Related U.S. Application Data

(60) Provisional application No. 62/693,693, filed on Jul. 3, 2018.

(51) Int. Cl.
*G16H 40/20* (2018.01)
*G06Q 30/04* (2012.01)
(Continued)

(52) U.S. Cl.
CPC ............ *G16H 40/20* (2018.01); *G06Q 30/04* (2013.01); *G06T 13/40* (2013.01); *G06T 19/006* (2013.01);
(Continued)

(58) Field of Classification Search
None
See application file for complete search history.

(56) References Cited

U.S. PATENT DOCUMENTS

| 5,377,319 A | 12/1994 | Kitahara et al. |
| 5,657,462 A | 8/1997 | Brouwer et al. |

(Continued)

FOREIGN PATENT DOCUMENTS

WO    WO2001/026059    4/2001

OTHER PUBLICATIONS

Takeda, Kazutaka, Koichi Kise, and Masakazu Iwamura. "Real-time document image retrieval on a smartphone." Document Analysis Systems (DAS), 2012 10th IAPR International Workshop on. IEEE, 2012.

(Continued)

*Primary Examiner* — Jeffrey J Chow
(74) *Attorney, Agent, or Firm* — Woods Oviatt Gilman LLP; Katherine H. McGuire, Esq.

(57) ABSTRACT

Systems and methods are presented for facilitating client reading and understanding of a billing statement. A client computing device includes a memory and a processor and a first set of computer instructions is stored in the memory of the client computing device and is executed by the processor of the client computing device. The computer instructions perform the steps of: receiving an electronic billing statement; identifying and highlighting select sections of the bill; launching a three-dimensional (3D) character; interposing the 3D character atop the electronic billing statement; and presenting a script via the 3D character, to the client, upon selection of a highlighted section. The script provides an explanation of the highlighted section and may be predefined or generated by artificial intelligence.

26 Claims, 7 Drawing Sheets

(51) Int. Cl.
  *G06T 13/40* (2011.01)
  *G06T 19/00* (2011.01)
  *H04N 5/232* (2006.01)
  *G06N 3/00* (2006.01)

(52) U.S. Cl.
  CPC ......... *H04N 5/23293* (2013.01); *G06N 3/006* (2013.01)

(56) References Cited

U.S. PATENT DOCUMENTS

| | | | |
|---|---|---|---|
| 5,903,896 A * | 5/1999 | Waldman | G06F 8/61 |
| 6,020,886 A | 2/2000 | Jacober et al. | |
| 6,993,719 B1 | 1/2006 | Edwards et al. | |
| 7,551,780 B2 | 6/2009 | Nudd et al. | |
| 7,751,805 B2 | 7/2010 | Neven et al. | |
| 7,818,183 B2 | 10/2010 | Schoenberg | |
| 8,000,979 B2 | 8/2011 | Blom | |
| 8,180,396 B2 | 5/2012 | Athsani et al. | |
| 8,506,377 B2 | 8/2013 | Heatherly | |
| 8,625,018 B2 | 1/2014 | Bilbrey et al. | |
| 8,811,711 B2 | 8/2014 | Calman et al. | |
| 9,007,364 B2 | 4/2015 | Bailey | |
| 9,030,495 B2 | 5/2015 | McCulloch et al. | |
| 9,081,473 B2 | 7/2015 | Nordstrom et al. | |
| 9,116,890 B2 | 8/2015 | King et al. | |
| 9,524,279 B2 | 12/2016 | Li et al. | |
| 9,996,211 B2 | 6/2018 | Sandler et al. | |
| 10,055,641 B2 | 8/2018 | Krishnan | |
| 10,068,378 B2 | 9/2018 | Cabanier et al. | |
| 10,068,380 B2 | 9/2018 | Chang et al. | |
| 10,225,521 B2 | 3/2019 | Gorodetski et al. | |
| 10,706,477 B1 * | 7/2020 | Le chevalier | G06Q 40/02 |
| 2009/0172516 A1 | 7/2009 | Gill | |
| 2010/0125790 A1 | 5/2010 | Erskin | |
| 2010/0164990 A1 | 7/2010 | Van Doorn | |
| 2013/0085935 A1 * | 4/2013 | Nepomniachtchi | G06K 9/38 705/40 |
| 2014/0188756 A1 | 7/2014 | Ponnavaikko | |
| 2014/0258889 A1 * | 9/2014 | Badge | G06F 16/954 715/760 |
| 2014/0310595 A1 | 10/2014 | Acharya et al. | |
| 2016/0012186 A1 | 1/2016 | Zasowski et al. | |
| 2016/0049010 A1 | 2/2016 | Hinski | |
| 2016/0132290 A1 * | 5/2016 | Raux | G06F 3/013 704/275 |
| 2016/0267808 A1 | 9/2016 | Agostini et al. | |
| 2019/0236594 A1 * | 8/2019 | Ehrlich-Quinn | G06Q 20/065 |
| 2019/0392018 A1 * | 12/2019 | Reedy | G06F 16/958 |
| 2020/0110930 A1 * | 4/2020 | Simantov | G06N 20/00 |

OTHER PUBLICATIONS

Fruend, Juergen, et al. "The augmented reality personal digital assistant." Proc. of 2nd Int. Symp. on Mixed Reality. 2001.

Hollerer, Tobias, Steven Feiner, and John Pavlik. "Situated documentaries: Embedding multimedia presentations in the real world." Wearable Computers, 1999. Digest of Papers. The Third International Symposium on. IEEE, 1999.

Erol, Berna, Emilio Antúnez, and Jonathan J. Hull. "HOTPAPER: multimedia interaction with paper using mobile phones." Proceedings of the 16th ACM international conference on Multimedia. ACM, 2008.

Rekimoto, Jun. "The magnifying glass approach to augmented reality systems." International Conference on Artificial Reality and Tele-Existence. vol. 95. 1995.

Alisa. "5 Business Use Cases for Augmented Reality" codeflugel. https://codefluegel.com/en/5-anwendungsbereiche-fuer-augmented-reality-in-unternehmen/.

Dang, Quoc Bao, et al. "Camera-based document image retrieval system using local features-comparing SRIF with LLAH, SIFT, SURF, and ORB." Document Analysis and Recognition (ICDAR), 2015 13th International Conference on. IEEE, 2015.

* cited by examiner

3D AUGMENTED REALITY DOCUMENT INTERACTION

TECHNICAL FIELD

The present invention relates to a system, method and device application for patient viewing and examining different parts of a healthcare provider (e.g., hospital) billing statement; and more particularly relates to a system, method and an Augmented Reality (AR) device application allowing patients to interact with a paper or electronic copy of a participating healthcare providers' billing statement through the mobile device's camera; and still more particularly to a system, method and device application that assists patients with reading and understanding the billing statement.

BACKGROUND OF THE INVENTION

Healthcare billing statements (such as those from hospitals, clinics, or doctor's offices) are notoriously difficult to read and understand for the average consumer/patient. For example, a healthcare billing statement is typically structured with several different sections having multiple service names and/or related procedures. Some, if not all, of the information may be in medical terms and/or codes not readily known to the average consumer (usually but not always the patient; the term "patient" will be used hereinafter for convenience). The patient is thus often overwhelmed upon receiving a billing statement and may not understand for what, exactly, they are being billed. This can cause dissatisfaction in the patient's financial experience and reflect poorly on the billing entity who otherwise strives for good customer relations. Presently available tools for helping the patient understand the bill amount to little more than referring the patient to other sources, such as FAQ's, glossaries or websites which are difficult to navigate or difficult to understand and/or simply provide a phone number for the patient to call into a contact center. The patient may likely be put on hold or transferred among different departments before any questions are answered. Thus, currently available billing statement help tools simply fail in delivering a satisfactory patient billing experience.

There therefore remains a need for a healthcare billing statement patient guidance solution which provides patient assistance in a pleasant, quick and otherwise satisfactory manner. The present invention addresses these, as well as other needs.

SUMMARY OF THE INVENTION

As will be described in more detail below, the present invention provides, in a first aspect, a downloadable, three-dimensional (3D) Augmented Reality application (hereinafter, the "Application") which is operable to recognize a healthcare billing statement of a participating healthcare provider by using the device's video input, such as a camera. Upon the Application recognizing the billing statement, an Augmented Reality experience begins for the patient. A 3D animated character virtually walks onto the billing statement as it appears on the Mobile device screen and turns to address the patient using a pre-recorded script. Using the mobile device touch screen, the patient can interact with sections of the billing statement by touching them. The virtual character (which may have a name, e.g., "Eve") walks to each billing statement section the patient touches. Eve explains that section of the billing statement, such as through use of a pre-recorded script or artificial intelligence (AI)-generated text. Eve invites the patient to use any of four (4) quick link buttons at the bottom of the mobile device screen to Pay the Bill online, Call the 1 billing contact center, email the billing care office or access the patient portal. The invention offers more opportunity for the patient to answer questions about their healthcare bill using a 3D animated experience, requiring less time on the patient's part to find answers and lowering the need for contact center interaction.

In another aspect, it should be understood that the methods set forth above may be embodied in computer readable instructions stored on a non-transitory computer readable medium.

Additional aspects, objects, advantages and novel features of the present invention will be set forth in part in the description which follows, and will in part become apparent to those in the practice of the invention, when considered with the attached figures.

DETAILED DESCRIPTION OF THE INVENTION

Figure 1:
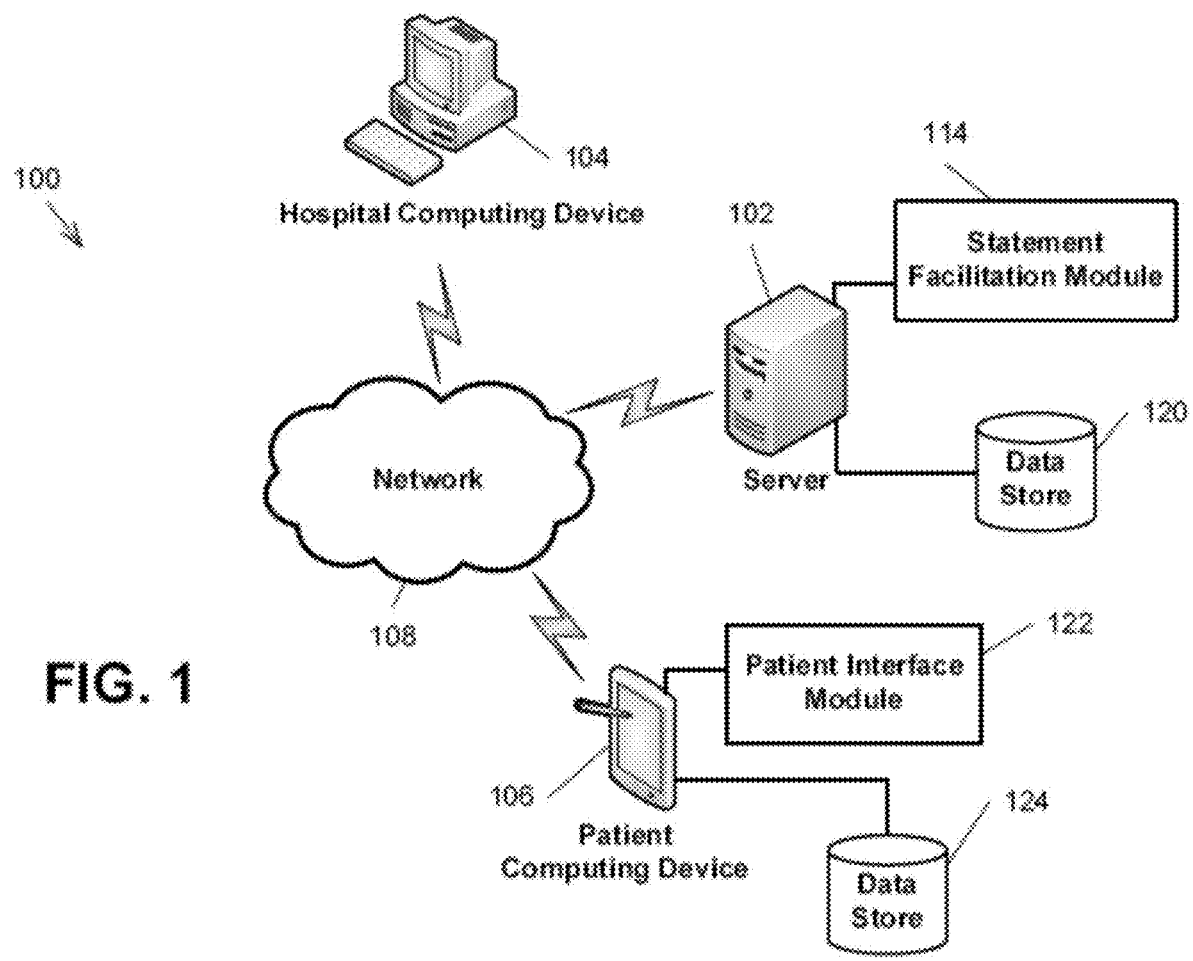
FIG. 1 is a schematic drawing showing an exemplary system that may be used to implement any of the methods or processing described herein in accordance with one aspect of the present invention.

Generally, the system, tools and methods described herein for facilitating patient viewing and understanding of healthcare bills may be implemented in hardware, software, and combinations thereof. Referring to the drawings in detail, and specifically to FIG. 1, reference numeral 100 generally designates an exemplary network environment in which a computer-implemented billing statement facilitation system in accordance with one aspect of the invention may be implemented. For instance, system 100 may include a server 102, a healthcare computing device 104, and a patient computing device 106 in communication with each other over a network 108. Network 108 may be any type of network, such as a wide area network or local area network that allows for wired and/or wireless communication between server 102 and computing devices 104, 106. It should be understood that server 102 and computing devices 104, 106, may be a desktop computer, smartphone, tablet, or any other type of mobile computing device that includes a processor configured for implementing computer-executable instructions and methods as described herein.

In accordance with an aspect of the present invention, server 102 includes a processor and a memory having a statement facilitation module 114 stored therein. Statement facilitation module 114 includes a first set of computer-executable instructions configured for performing, through the use of the processor, a number of algorithmic steps that facilitate the statement facilitation process. In particular, statement facilitation module 114 may be a cloud-based software platform that is accessible by patient computing device 106 over network 108. Patient computing device 106 utilizes statement facilitation module 114 to, among other things, allow for the communication of a patient billing statement from patient computing device 106 to a data store/memory 120 of server 102 as will be described in greater detail below.

In a further aspect, as best seen in FIG. 1, the present invention includes a patient interface module 122 including a second set of computer executable instructions stored in a memory of patient computing device 106. Patient interface module 122 includes computer executable instructions configured for performing, through the use of the processor of patient computing device 106, a number of algorithmic steps that facilitate the statement facilitating process when used in conjunction with statement facilitation module 114. Patient interface module 122 may be in the form of a mobile software application (i.e., mobile app) or any other type of software program that can be easily downloaded and used by a patient to interact with server 102.

In one aspect of the present invention, an Augmented Reality (AR) device application (the "Application") powered by a host, such as Avadyne Health of Moline, Ill., is used by participating healthcare providers and their patients to interact with a paper or an electronic copy of a healthcare bill or healthcare statement using patient computing device's 106 video input, such as a camera. As used herein, "healthcare bill," "healthcare statement" and/or "healthcare billing statement" applies to any healthcare- or medical-related communications, such as but not limited to those received from a hospital, clinic, doctor's office, urgent care office, dentist's office or other medical professionals. The Application may use the Unity® game engine by Unity Technologies as the framework. Unity allows the integration and use of other technologies to create a fully animated and interactive/touch screen experience. Unity integrates with Vuforia® by PTC Inc., an Augmented Reality engine to support media (healthcare billing statement) recognition via the device's camera and define the position and movement of a 3D animated character. It should be noted that, while specific examples of a game engine and AR engine have been provided, any suitable engine may be utilized and are to be considered within the teachings of the present invention.

Figure 2:
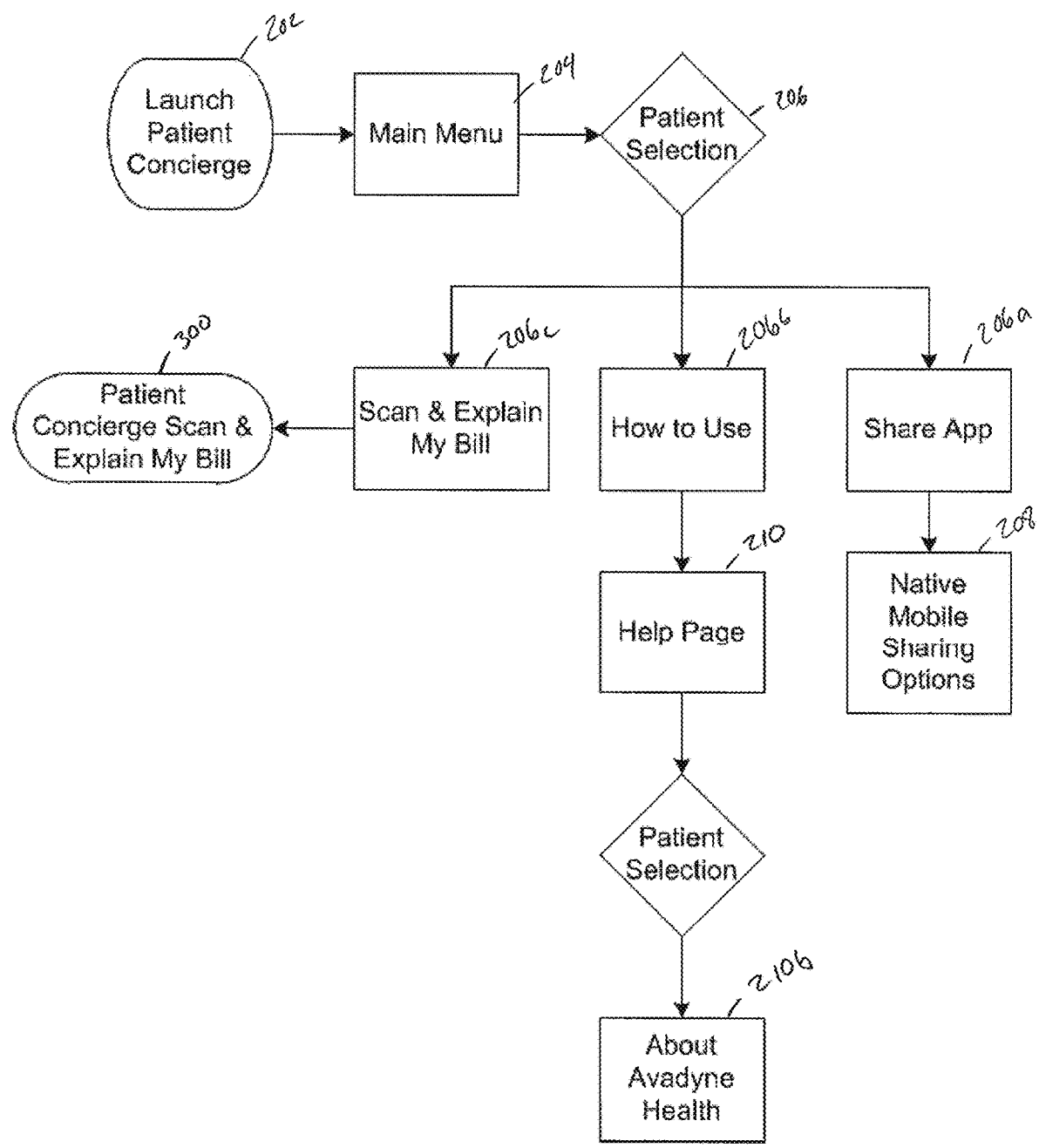
FIG. 2 is a flow diagram of an embodiment of the Application launch process.
Figure 3:
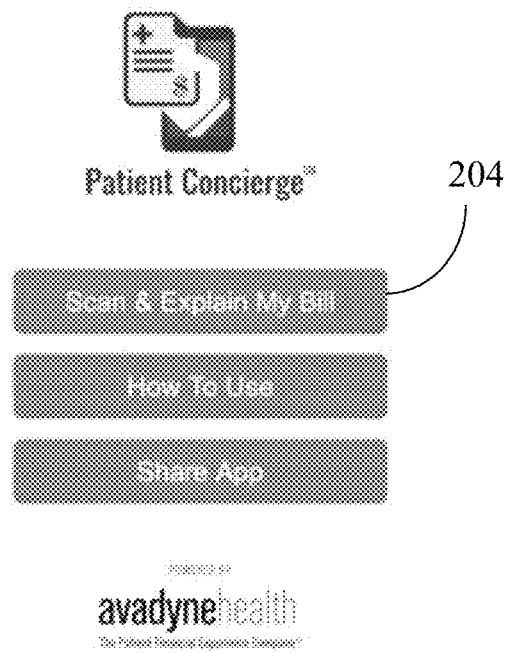
FIG. 3 is a graphic representation of an embodiment of the Application Main Menu page offering a plurality of options.

FIG. 2 shows the basic operational flow of launching and navigating the main menu options that may be provided by patient interface module 122. Patient interface module 122 may be configured for processing an algorithm that facilitates patient understanding of a healthcare billing statement. Assuming that the Application user (patient) has downloaded and installed the Application on patient computing device 106, the patient initially opens the Application by tapping an Application icon 202, for instance "Patient Concierge", whereupon the Main Menu 204 appears on the device's screen, see FIG. 3, for example.

Figure 4:
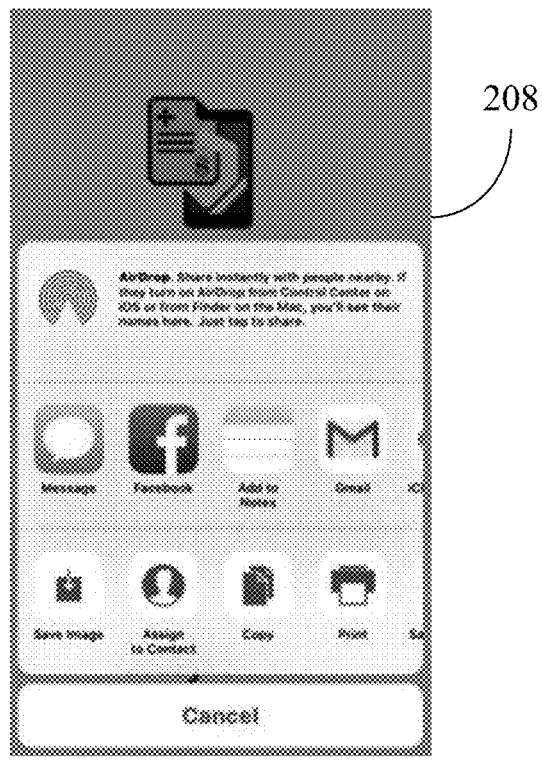
FIG. 4 is a graphic representation showing an embodiment of the native device functions menu which may be used to share the Application with others.
Figure 5:
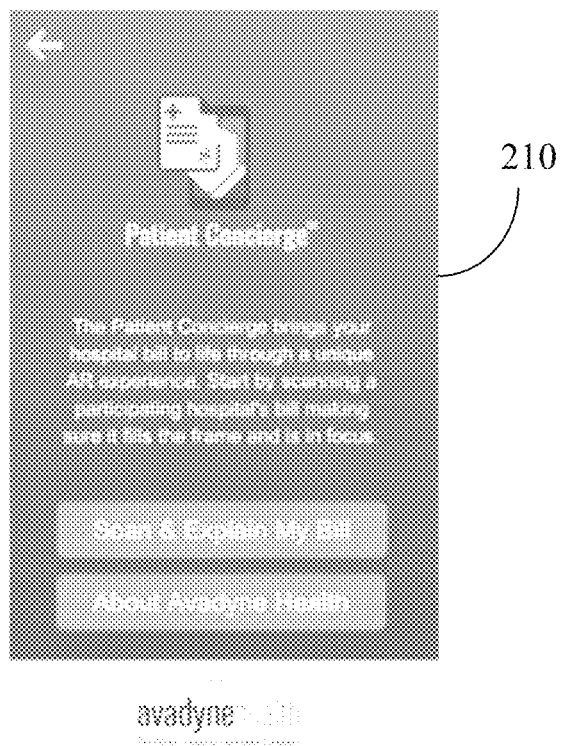
FIG. 5 is a graphic representation showing an embodiment of an options page.

In accordance with an aspect of the invention, the patient may then, for instance, select from a plurality of options 206. By way of example and without limitation thereto, options may include: (1) a "Share App" button 206a that allows patient computing device 106 to share the application. Sharing will send a link to the specific store where the user downloaded the Application. FIG. 4 shows a "share page" 208 on an iOS device screen as an example; (2) a "How to Use" button 206b selection opens a help page 210, as shown in FIG. 5 for example, indicating how to setup and use the Patient Concierge Application; (3) an "About" page 210b may redirect the patient to the host's default web browser (e.g., Avadyne Health), see also FIG. 6, such as via network 108 and server 102; and (4) a "Scan & Explain My Bill" button 206c selection accesses the key functionalities of the Application as will be described in greater detail below.

Figure 6:
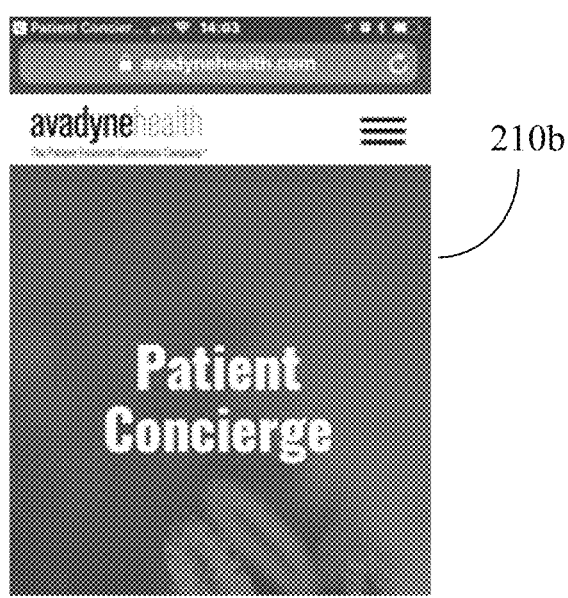
FIG. 6 is a graphic representation showing an embodiment of the Application's company website home page.
Figure 7:
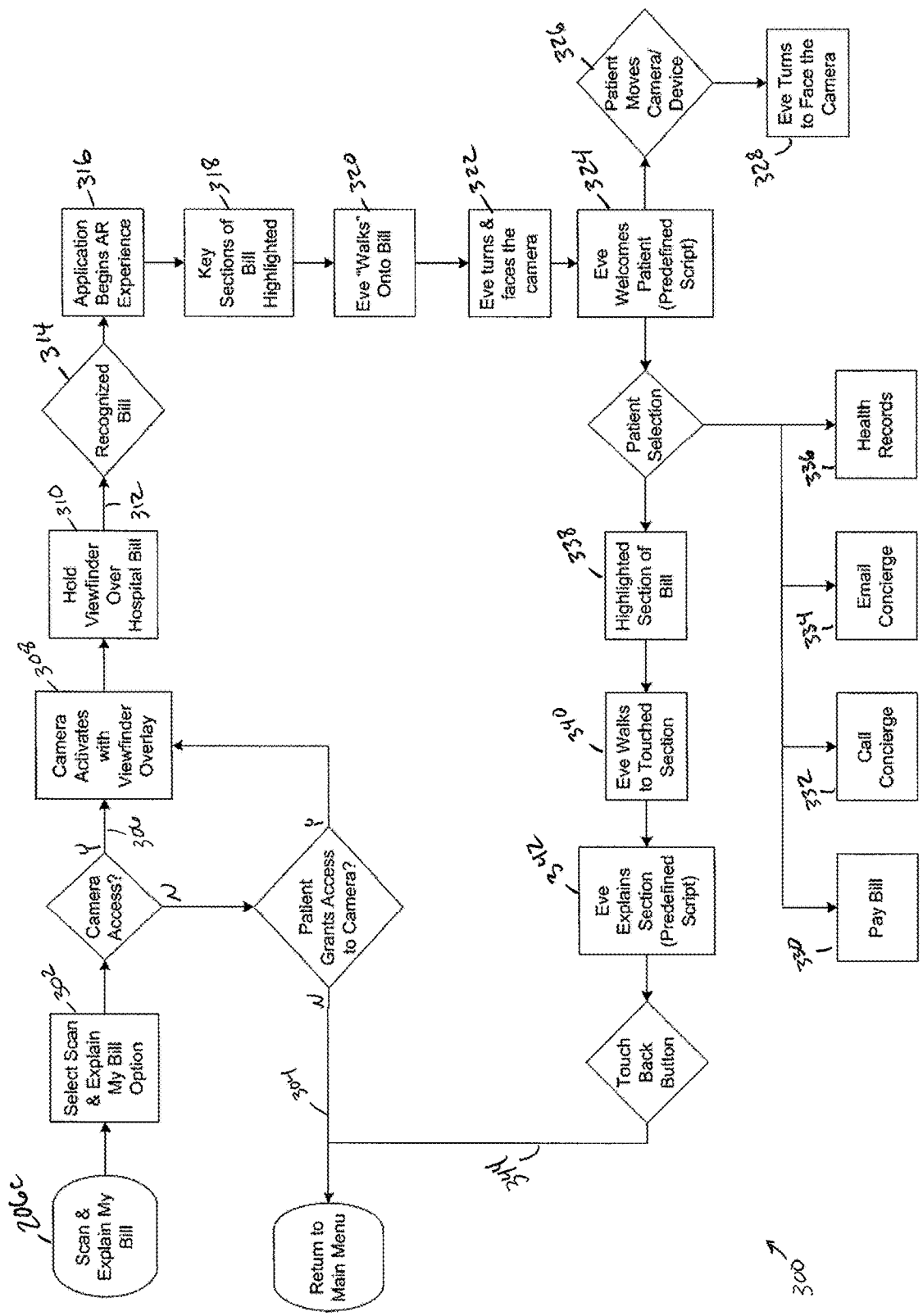
FIG. 7 is a flow diagram of an embodiment of the software Application interactive module functionality.

A flow diagram of the Scan & Explain My Bill functionality is seen in FIG. 7. The Scan & Explain My Bill utilizes patient interface module 122 to either instruct the camera of patient computing device 106 to acquire an image of a patient billing statement or to recognize an electronic file of a billing statement from a participating healthcare provider. As shown in FIG. 6, at step 302, patient interface module 122 is configured to implement the Scan & Explain My Bill algorithm 300 by initially asking for access to the device's camera if scanning a paper copy of a statement and access has not already been granted. If access is not given, algorithm 300 returns to the main menu at step 304. If access is (or has already been) granted, algorithm 300 accesses the camera at step 306. At step 308, the device screen of patient interface module 122 displays guides for the patient to use the camera as a viewfinder to scan the billing statement. The patient holds the camera over the billing statement using the viewfinder as a guide at step 310. At step 312, algorithm 300 scans the billing statement using the device's camera. If the statement is recognized by algorithm 300 (step 314), algorithm 300 then starts an AR experience at step 316.

For the patient, the AR experience begins when important sections of the billing statement are highlighted by algorithm 300 to indicating on the device's touch screen where the patient can tap a section of the bill (step 318), followed by introduction of an animated character (e.g., named "Eve" in this embodiment) at step 320. Algorithm 300 may then direct Eve to face the patient (step 322) and welcome the patient to the Application by presenting a script (audio file) at step 324. This script may be predetermined or generated by artificial intelligence (AI). In one aspect of the invention, Application 100 may interrogate the multi-axis motion sensor (e.g., 6- or 9-axis) of patient computing device 106 at step 326 so that Eve may be continually repositioned (step 328) to directly address the patient should the device be moved or tilted.

Once Eve has been introduced by algorithm 300, algorithm 300 is configured to present the patient with a plurality of selections. By way of example and without limitation thereto, algorithm 300 may access patient computing device 106 functionality through quick links, thereby allowing the patient to Pay Bill (redirection to Payment portal thru web browser via network 108) (step 330); Call Concierge (redirect to phone app with predefined phone number) (step 332); Email Concierge (redirect to default email with predefined email address) (step 334), such as through server 102 via network 108; and Hospital/Health Records (redirect to web browser with predefined provider patient portal) (step 336), such as via computing device 104 and server 102. It should be noted that the above steps 330-336 are exemplary and additional or alternative quick links/steps may be provided without deviating from the present invention.

Additionally or alternatively, should the patient have a question or would like more information regarding the billing statement, at step 338 the patient may select, such as via the device's touch screen, a highlighted section of the bill on the device (e.g., such as those areas highlighted during step 318). Algorithm 300 is configured to have Eve "walk" to the selected area (step 340) and provide an explanation of the selected region. By way of example and without limitation thereto, Eve may use a predefined script or AI-generated text (step 342). Once the explanation is finished or the patient touches the "back" button, algorithm 300 returns to the main menu (step 344).

Figure 8:
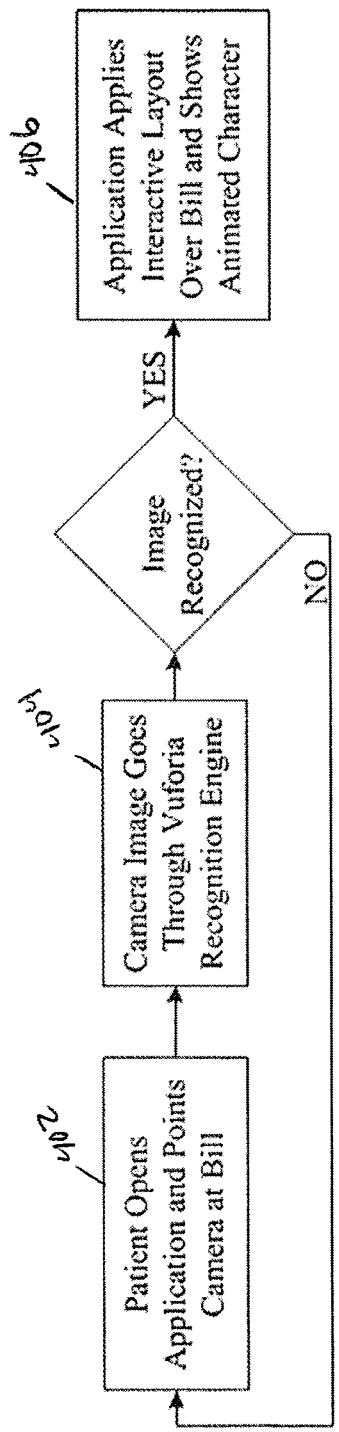
FIG. 8 is a flow diagram of an exemplary bill recognition function.

In one aspect of the present invention, algorithm 300 may include the Unity 3D Game engine ("Unity") and the Vuforia Augmented Reality (AR) engine ("Vuforia"). The Unity engine supports the Application framework and allows algorithm 300 to integrate all components of the Application. The Vuforia engine interacts with Unity and uses the camera to receive information. With reference to FIG. 8, a patient initially opens the Application and points the device's camera at the healthcare billing statement (step 402). At step 404, Vuforia uses the data received from the camera to track and recognize the surface of the image (in this case, the healthcare billing statement). When Vuforia successfully recognizes a healthcare billing statement, the visuals are displayed as a single, 3D scene which is displayed on the surface of the healthcare billing statement (step 406).

The Vuforia engine activates components of the Augmented Reality experience as follows: a) positions the internal 3D scene in order to synchronize the camera point of view with device camera. This gives the 3D effect and through the device viewer, gives the patient the experience that they are seeing an animated character standing on the surface of the bill; b) position the recognized image in virtual 3D, setting the beginning coordinate point 0,0,0 (x,y,z) for the animated character. This sets the center point for the image (billing statement) so no matter where the camera moves, the Patient Concierge Application is always aware of the locations/sections of the image (billing statement); and c) triggers Unity custom functionality to superimpose a predefined layout to the billing statement.

Given the positioning of the image at 0,0,0 coordinates, Vuforia applies a clickable layover to the healthcare billing statement image, maintaining its position at all times. This allows the patient to move the camera around without moving the highlighted regions of the image. Vuforia also places the animated character on the screen using predefined coordinates. The animated character is set to an anchor point (center of the billing statement) at the start. Unity custom programming may then be applied to the layover, allowing touch interaction with the billing statement image. Touching the section of the overlay moves the animated character to predefined coordinates within that section of the image. Unity and Vuforia engines are designed to allow the patient to "skip" sections, i.e., tap a new section and animation/speech will stop and move to the next section. In one aspect of the present invention, images, animations and voice-overs are embedded in the application allowing for quick, uninterrupted and offline interaction with a billing statement.

In accordance with further aspects of the present invention, algorithm 300 may provide for additional functionalities, such as but not limited to scanning and recognition of physician bills, scanning and recognition of Explanations of Benefits (EOBs), scanning and recognition of Medicare EOBs, scanning and recognition of Commercial Insurance EOBs, scanning and recognition of other healthcare related bills, scanning and recognition of defined healthcare logos or images provider information such as phone number, website address and physical locations, scanning and recognition of prescriptions for drug facts/interactions, and scanning and recognition of government healthcare logos for information on financial assistance.

In another aspect, it should be understood that the methods set forth above may be embodied in computer readable instructions stored on a non-transitory computer readable medium.

Having described embodiment number of aspects of the system and associated methods, an exemplary computer environment for implementing the system is presented next.

Figure 9:
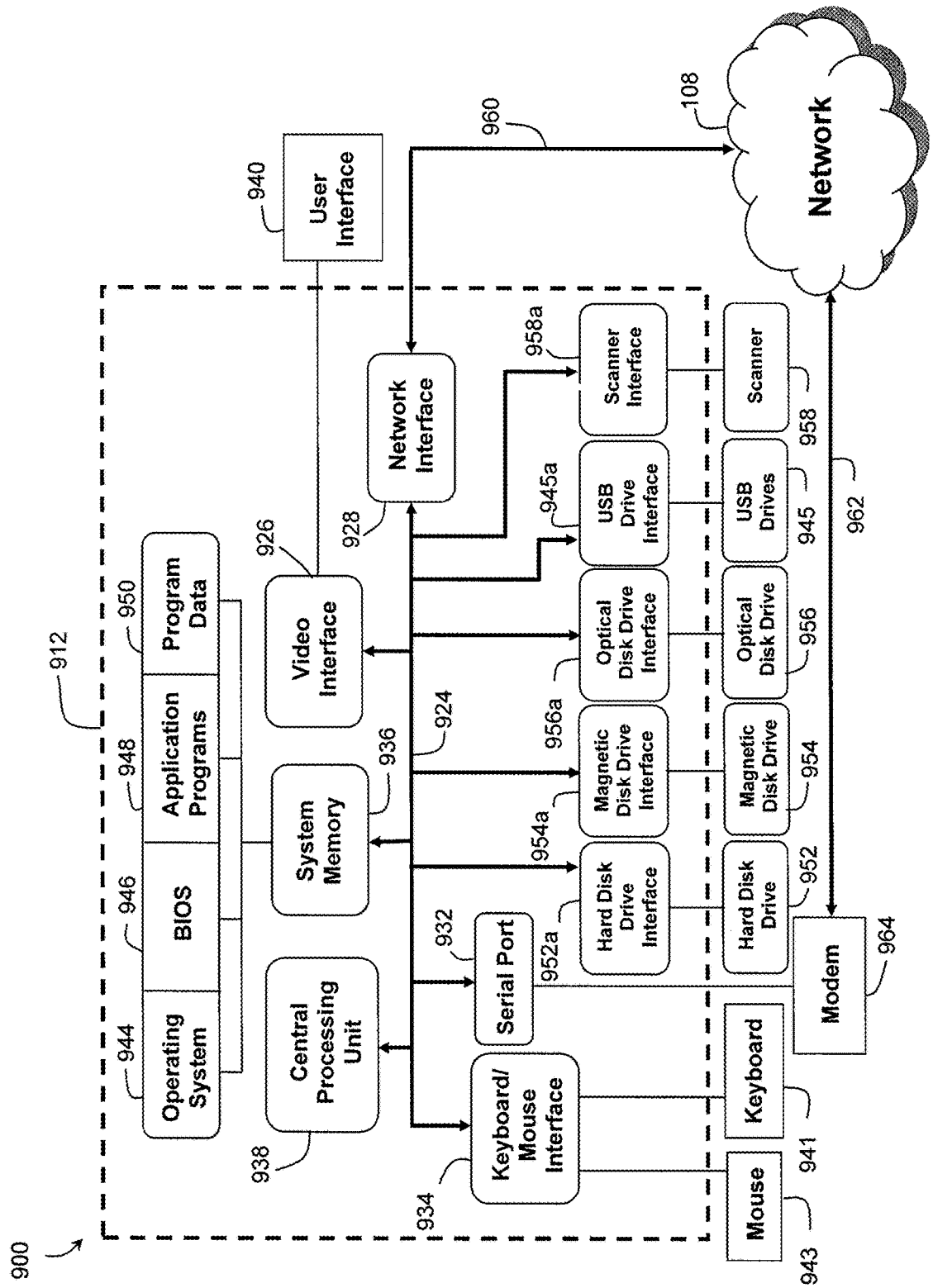
FIG. 9 is a block diagram generally illustrating a computing environment in which the invention may be implemented.

FIG. 9 shows an exemplary computing environment 900 that may be used to implement any of the processing of computer-executable instructions thus far described. Computing environment 900 may be a computer 912 that is representative of server 102, healthcare computing device 104 or patient computing device 106. For example, computer 912 may include a system bus 924 that couples a video interface 926, network interface 928, one or more serial ports 932, a keyboard/mouse interface 934, and a system memory 936 to a Central Processing Unit (CPU) 938. A monitor or display 940 is connected to bus 924 by video interface 926 and provides the user with a graphical user interface to perform all of the relevant functionality described above. The graphical user interface allows the user to enter commands and information into computer 912 using a keyboard 941 and a user interface selection device 943, such as a mouse, touch screen or other pointing device. Keyboard 941 and user interface selection device are connected to bus 924 through keyboard/mouse interface 934. Display 940 and user interface selection device 943 are used in combination to form the graphical user interface which may allow the user to implement at least a portion of the processes described above with respect to statement facilitation module 114 and/or patient interface module 122. Other peripheral devices may be connected to computer through serial port 932 or universal serial bus (USB) drives 945 to transfer information to and from computer 912.

The system memory 936 is also connected to bus 924 and may include read only memory (ROM), random access memory (RAM), an operating system 944, a basic input/output system (BIOS) 946, application programs 948 and program data 950. The computer 912 may further include a hard disk drive 952 for reading from and writing to a hard disk, a magnetic disk drive 954 for reading from and writing to a removable magnetic disk (e.g., floppy disk), and an optical disk drive 956 for reading from and writing to a removable optical disk (e.g., CD ROM or other optical media). The computer 912 may also include USB drives 945 and other types of drives for reading from and writing to flash memory devices (e.g., compact flash, memory stick/PRO and DUO, SD card, multimedia card, smart media xD card), and a scanner 958. A hard disk interface 952a, magnetic disk drive interface 954a, an optical drive interface 956a, a USB drive interface 945a, and a scanner interface 958a operate to connect bus 924 to hard disk drive 952, magnetic disk drive 954, optical disk drive 956, USB drive 945 and a scanner 958, respectively. Each of these drive components and their associated computer-readable media may provide computer 912 with non-volatile storage of computer-readable instruction, program modules, data structures, application programs, an operating system, and other data for the computer 912. In addition, it will be understood that computer 912 may also utilize other types of computer-readable media in addition to those types set forth herein, such as digital video disks, random access memory, read only memory, other types of flash memory cards, magnetic cassettes, and the like.

As mentioned above, statement facilitation module 114 may be implemented in a networked environment using logical connections to establish communication between server 102, healthcare processor computing device 104 and/or patient computing device 106, as previously described. Network interface 928 provides a communication path 960 between bus 924 and network 108, which allows the instructions, modules, data, sequences, files, designations, notifications, or information described above to be communicated through network 108 between server 102, healthcare processor computing device 104 and/or patient computing device 106 using computer 912, as described above. This type of logical network connection is commonly used in conjunction with a local area network (LAN). The instructions, modules, data, sequences, files, designations, notifications, or information may also be communicated from bus 924 through a communication path 962 to network 108 using serial port 932 and a modem 964. Using a modem connection is commonly used in conjunction with a wide area network (WAN). It will be appreciated that the network connections shown herein are merely exemplary, and it is within the scope of the present invention to use other types of network connections between server 102, healthcare processor computing device 104 and/or patient computing device 106, including both wired and wireless connections.

While the above discussion referenced healthcare bills and patients as a specific example, the methods and systems described may be used with any suitable billing statement system and its associated clients and that such additional applications are to be considered within the teachings of the present invention.

From the foregoing, it will be seen that this invention is one well adapted to attain all the ends and objects hereinabove set forth together with other advantages which are obvious and which are inherent to the system and method. It will be understood that certain features and sub combinations are of utility and may be employed without reference to other features and sub combinations. This is contemplated by and is within the scope of the claims. Since many possible embodiments of the invention may be made without departing from the scope thereof, it is also to be understood that all matters herein set forth or shown in the accompanying drawings are to be interpreted as illustrative and not limiting.

The constructions described above and illustrated in the drawings are presented by way of example only and are not intended to limit the concepts and principles of the present invention. As used herein, the terms "having" and/or "including" and other terms of inclusion are terms indicative of inclusion rather than requirement.

While the invention has been described with reference to preferred embodiments, it will be understood by those skilled in the art that various changes may be made and equivalents may be substituted for elements thereof to adapt to particular situations without departing from the scope of the invention. Therefore, it is intended that the invention not be limited to the particular embodiments disclosed as the best mode contemplated for carrying out this invention, but that the invention will include all embodiments falling within the scope and spirit of the appended claims.

What is claimed is:

1. A system for facilitating user reading and understanding of a statement, the system comprising:
   a user computing device including a memory and a processor; and
   a first set of computer instructions configured for being executed by the processor of the user computing device to perform the steps of:
   receiving an electronic statement;
   identifying and highlighting select sections of the statement;
   launching a three-dimensional (3D) animated character;
   interposing the 3D animated character atop the electronic statement;
   moving the 3D animated character proximate to a location of a user-selected highlighted section of the electronic statement; and
   presenting a script via the 3D animated character, to the user, of the user-selected highlighted section;
   wherein the script provides an explanation of the user-selected highlighted section.

2. The system of claim 1 wherein the first set of computer instructions is further configured for performing the step of:
   continually repositioning the 3D animated character upon movement or tilting of the user computing device so that the 3D animated character is always facing the user.

3. The system of claim 1 further comprising:
   a server including a server memory and a server processor, wherein the server is in communication with a computing device and the user computing device over a network.

4. The system of claim 3 wherein the step of receiving the electronic statement includes downloading the electronic statement from the computing device via the network.

5. The system of claim 1 wherein the step of receiving the electronic statement includes:
   receiving a hardcopy statement;
   accessing a camera on the user computing device;
   acquiring a digital image of the hardcopy statement.

6. The system of claim 5 wherein the camera presents a viewfinder overlay atop the statement.

7. The system of claim 3 wherein the step of receiving the electronic statement includes:
   receiving a hardcopy statement;
   accessing a camera on the user computing device;
   acquiring a digital image of the hardcopy statement.

8. The system of claim 7 wherein a second set of computer instructions that when executed by the server processor performs the steps of:
   receiving the digital image of the statement from the user computing device; and
   providing the script for the user-selected highlighted section to the user computing device for presentation by the 3D animated character.

9. The system of claim 1 wherein the user computing device is a personal computer, laptop computer, tablet computer or smartphone.

10. The system of claim 1 wherein the script is a predefined script or is text generated by artificial intelligence.

11. The system of claim 1 wherein the statement is a billing statement.

12. The system of claim 11 wherein the billing statement is a healthcare billing statement.

13. The system of claim 2 wherein said 3D animated character is in the form of a person having a face which automatically repositions itself to face the user in response to movement or tilting of the user computing device.

14. A method for facilitating user reading and understanding of a statement comprising the steps of:
   receiving an electronic statement using a user computing device;
   identifying and highlighting select sections of the statement;

launching a three-dimensional (3D) animated character;
interposing the 3D animated character atop the electronic statement;
moving the 3D animated character proximate to a location of a user-selected highlighted section of the electronic statement; and
presenting a script via the 3D animated character, to the user, of the user-selected highlighted section;
wherein the script provides an explanation of the user-selected highlighted section.

15. The method of claim 14 wherein the first set of computer instructions is further configured for performing the step of:
continually repositioning the 3D animated character upon movement or tilting of the user computing device so that the 3D animated character is always facing the user.

16. The method of claim 14 further comprising:
a server including a server memory and a server processor, wherein the server is in communication with a computing device and the user computing device over a network.

17. The method of claim 16 wherein the step of receiving the electronic statement includes downloading the electronic statement from the computing device via the network.

18. The method of claim 14 wherein the step of receiving the electronic statement includes:
receiving a hardcopy statement;
accessing a camera on the user computing device;
acquiring a digital image of the hardcopy statement.

19. The method of claim 18 wherein the camera presents a viewfinder overlay atop the hardcopy statement.

20. The method of claim 16 wherein the step of receiving the electronic statement includes:
receiving a hardcopy statement;
accessing a camera on the user computing device;
acquiring a digital image of the hardcopy statement.

21. The method of claim 20 wherein a second set of computer instructions that when executed by the server processor performs the steps of:
receiving the digital image of the statement from the user computing device; and
providing the script for the selected section to the user computing device for presentation by the 3D animated character.

22. The method of claim 14 wherein the user computing device is a personal computer, laptop computer, tablet computer or smartphone.

23. The method of claim 14 wherein the script is a predefined script or is text generated by artificial intelligence.

24. The method of claim 14 wherein the statement is a billing statement.

25. The method of claim 24 wherein the billing statement is a healthcare billing statement.

26. The method of claim 15 wherein said 3D animated character is in the form of a person having a face which automatically repositions itself to face the user in response to movement or tilting of the user computing device.

* * * * *